United States Patent
Pratt et al.

(10) Patent No.: US 10,054,564 B2
(45) Date of Patent: Aug. 21, 2018

(54) SYSTEMS AND METHODS OF FAST POWER UP FOR ELECTROCHEMICAL SENSORS

(71) Applicant: Life Safety Distribution AG, Hegnau (CH)

(72) Inventors: Keith Francis Edwin Pratt, Portsmouth (GB); Ali Hosseinmardi, Portsmouth (GB)

(73) Assignee: Life Safety Distribution AG, Hegnau (CH)

( * ) Notice: Subject to any disclaimer, the term of this patent is extended or adjusted under 35 U.S.C. 154(b) by 618 days.

(21) Appl. No.: 13/944,375

(22) Filed: Jul. 17, 2013

(65) Prior Publication Data

US 2014/0021064 A1 Jan. 23, 2014

Related U.S. Application Data

(60) Provisional application No. 61/674,042, filed on Jul. 20, 2012.

(51) Int. Cl.
*G01N 27/416* (2006.01)
*G01N 27/406* (2006.01)

(52) U.S. Cl.
CPC ....... *G01N 27/416* (2013.01); *G01N 27/4065* (2013.01)

(58) Field of Classification Search
CPC ............. G01N 27/416; G01N 27/4163; G01N 27/4065; G01N 27/28; G01N 27/283; G01N 27/407–27/41

See application file for complete search history.

(56) References Cited

U.S. PATENT DOCUMENTS

| | | | |
|---|---|---|---|
| 4,315,753 A | 2/1982 | Bruckenstein et al. | |
| 5,180,968 A | 1/1993 | Bruckenstein et al. | |
| 6,428,684 B1* | 8/2002 | Warburton | G01N 27/4163 204/401 |
| 8,317,998 B2 | 11/2012 | Pratt et al. | |
| 2004/0251144 A1* | 12/2004 | Chapples et al. | 205/775 |
| 2006/0081470 A1* | 4/2006 | Kaiser | 204/406 |

(Continued)

FOREIGN PATENT DOCUMENTS

| | | |
|---|---|---|
| EP | 2 239 562 A1 | 10/2010 |
| EP | 2687842 B1 | 9/2016 |

(Continued)

OTHER PUBLICATIONS

European Search Report, dated Sep. 23, 2013, corresponding to Application No. EP 13 17 7139.

(Continued)

*Primary Examiner* — Maris R Kessel
(74) *Attorney, Agent, or Firm* — Wick Phillips Gould & Martin, LLP

(57) ABSTRACT

Systems and methods of fast power up for electrochemical sensors are provided. A system can include an electrochemical sensor, and a potentiostat circuit, wherein, upon startup, the potentiostat circuit drives the electrochemical sensor to the electrochemical sensor's normal operating condition at a rate that is not limited by voltage and/or current supply. A method can include a potentiostat circuit driving an electrochemical sensor to the electrochemical sensor's normal operating condition at a rate that is not limited by voltage and/or current supply.

15 Claims, 14 Drawing Sheets

(56) References Cited

U.S. PATENT DOCUMENTS

| | | | |
|---|---|---|---|
| 2006/0091007 A1* | 5/2006 | Inoue | G01N 27/4175 204/406 |
| 2008/0251379 A1* | 10/2008 | Mayer | 204/406 |
| 2010/0252455 A1 | 10/2010 | Pratt et al. | |
| 2010/0288652 A1* | 11/2010 | Pratt | G01N 27/4163 205/785.5 |

FOREIGN PATENT DOCUMENTS

| | | |
|---|---|---|
| GB | 2 340 612 A | 2/2000 |
| WO | WO 94/04912 | 3/1994 |

OTHER PUBLICATIONS

P. Grundler et al., Simultaneous joule heating and potential cycling of cylindrical microelectrodes, Analytica Chimica Acta, Apr. 1, 1995, vol. 305, No. 1-3, pp. 232-240.

Falko Wachholz et al., A Compact and Versatile Instrument for Radio Frequency Heating in Nonisothermal Electrochemical Studies, Wiley InterScience, Electroanalysis 19, 2007, No. 5, 535-540, www.electroanalysis.wiley-ych.de.

Potentiostat stability mystery explained, BioLogic Science Instruments, Application Note #4, Oct. 25, 2010.

Europe Patent Application No. 13177139.6, European Search Report, dated Oct. 7, 2013, 4 pages.

Europe Patent Application No. 13177139.6, Communication pursuant to Article 94(3) EPC, dated Oct. 8, 2013, 5 pages.

Europe Patent Application No. 13177139.6, Communication pursuant to Article 94(3) EPC, dated Apr. 4, 2014, 5 pages.

Europe Patent Application No. 13177139.6, Communication pursuant to Article 94(3) EPC, dated Nov. 10, 2014, 3 pages.

Europe Patent Application No. 13177139.6, Intention to Grant, dated Apr. 29, 2015, 35 pages.

Europe Patent Application No. 13177139.6, Decision to Grant, dated Aug. 20, 2015, 2 pages.

* cited by examiner

BC338 and BC337 transistors in booster circuit

Shorting switch for sensing electrode

Vo = IRS-RS, R1-R2-R3-R4


SYSTEMS AND METHODS OF FAST POWER UP FOR ELECTROCHEMICAL SENSORS

CROSS-REFERENCE TO RELATED APPLICATIONS

This application claims priority to U.S. Provisional Patent Application No. 61/674,042 filed Jul. 20, 2012 and titled "Systems and Methods of Fast Power Up for Electrochemical Sensors". U.S. Application No. 61/674,042 is hereby incorporated by reference.

FIELD

The present invention relates generally to electrochemical sensors. More particularly, the present invention relates to systems and methods of fast power up for electrochemical sensors.

BACKGROUND

Known biased electrochemical gas sensors typically require a prolonged stabilization time when powered up if the sensor, for example, has been left off load for a period of time. This is an issue for oxygen pump sensors, in particular, because oxygen sensors require power during normal operation since the target gas is usually present.

When known oxygen sensors are left unpowered, they no longer consume oxygen, and the oxygen builds up inside of the gas and liquid phase regions of the sensor, resulting in a large transient current upon power up. This process is described in U.S. application Ser. No. 12/754,023, which is assigned to the assignee hereof. The net result is that the sensor does not reach its optimum performance for a period of time after powering up.

For example, FIG. 1 is a graph 100 that illustrates the startup transient behavior of a known electrochemical oxygen pump sensor that has been off load for multiple days. Specifically, the graph 100 illustrates the stabilization time for such sensors that include a known potentiostat circuit, running on a +/−15V power supply, where the sensors are biased to a −600 mV vs internal platinum pseudo reference electrode, where the nominal sensor output is 400-500 µA in air, and where the sensors have been off load for multiple days.

Known potentiostat circuits often include a 10 Ohm resistor in series with the sensing electrode. For example, FIG. 2A is a circuit diagram of a known potentiostat circuit 200, FIG. 2B is a circuit diagram of a known current follower 210, and FIG. 2C is a circuit diagram of a circuit 220 approximately equivalent to a known electrochemical sensor.

FIG. 3 is a graph 300 that includes the data from the graph 100 plotted on a log scale. The data plotted on a log scale should illustrate a linear behavior if the transient current has a first order exponential decay. However, as seen in FIG. 3, linear behavior is only observed from about approximately 100-150 seconds and onwards by which time the error in air is already approximately 0.1-1% oxygen. Conversely, anomalous behavior is observed prior to 150 seconds even though the signal is saturated at approximately 40-100 seconds and then begins to decay.

In view of the above, there is a continuing, ongoing need for improved systems and methods of fast power up for electrochemical sensors.

DETAILED DESCRIPTION

Figure 1:
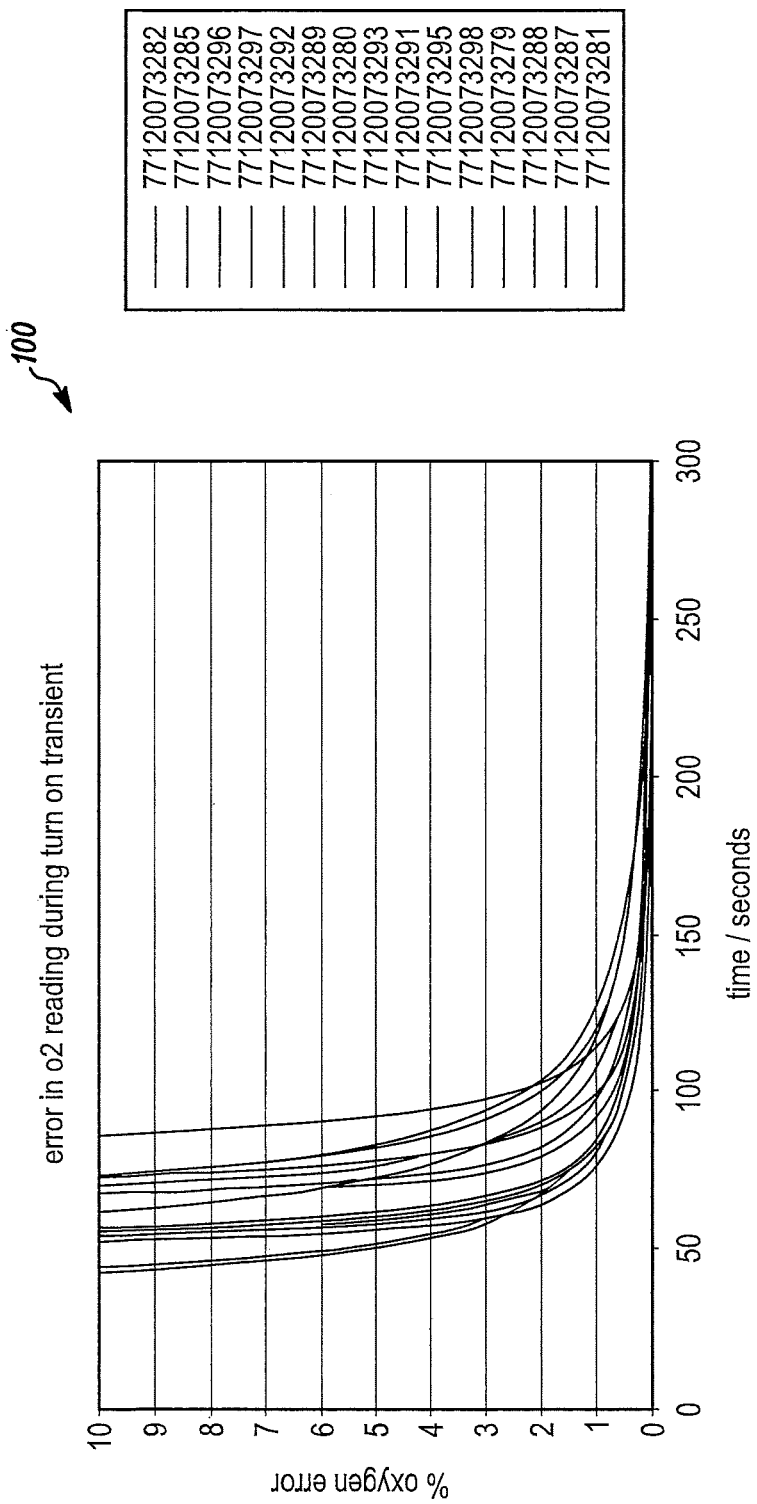
FIG. 1 is a graph that illustrates the startup transient behavior of a known electrochemical oxygen gas pump sensor that has been off load for multiple days.
Figure 2A:
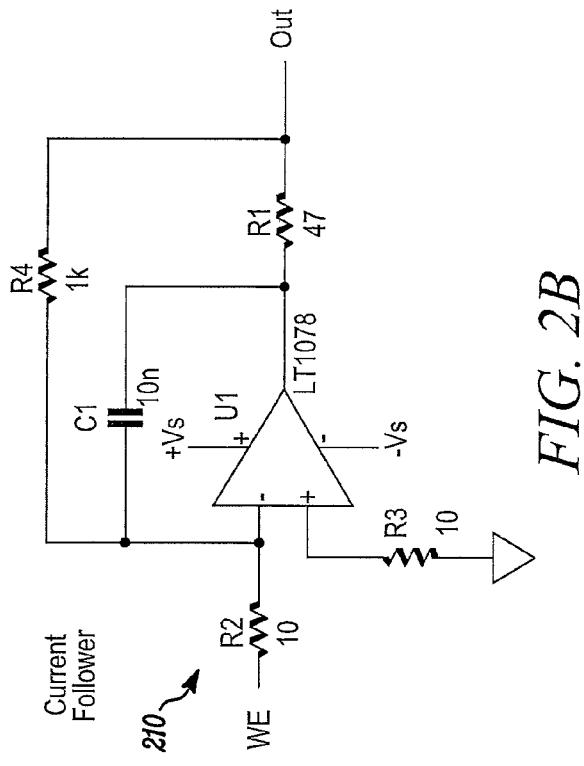
FIG. 2A is a circuit diagram of a known potentiostat circuit.
Figure 2B:
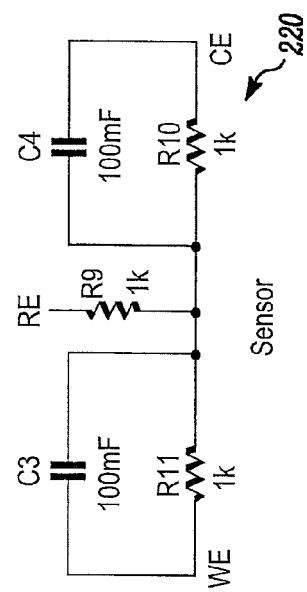
FIG. 2B is a circuit diagram of a known current follower.
Figure 2C:
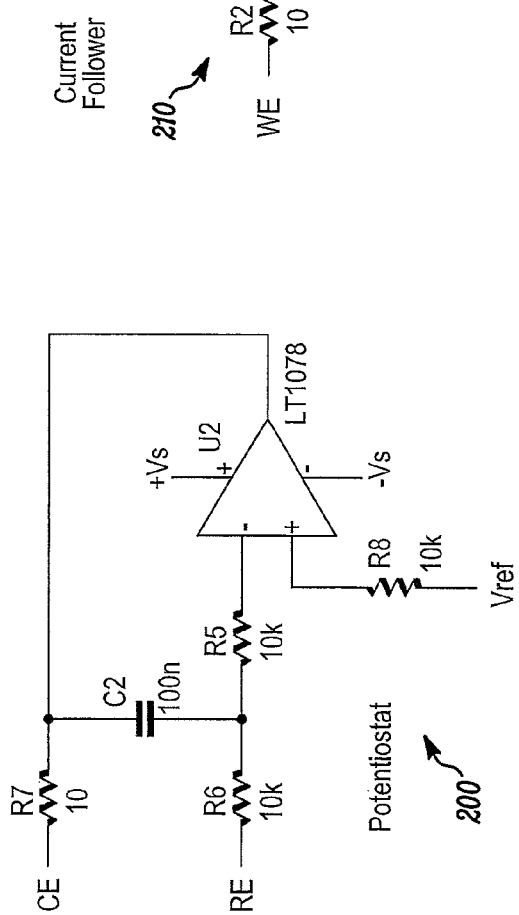
FIG. 2C is a circuit diagram of a circuit approximately equivalent to a known electrochemical sensor.
Figure 3:
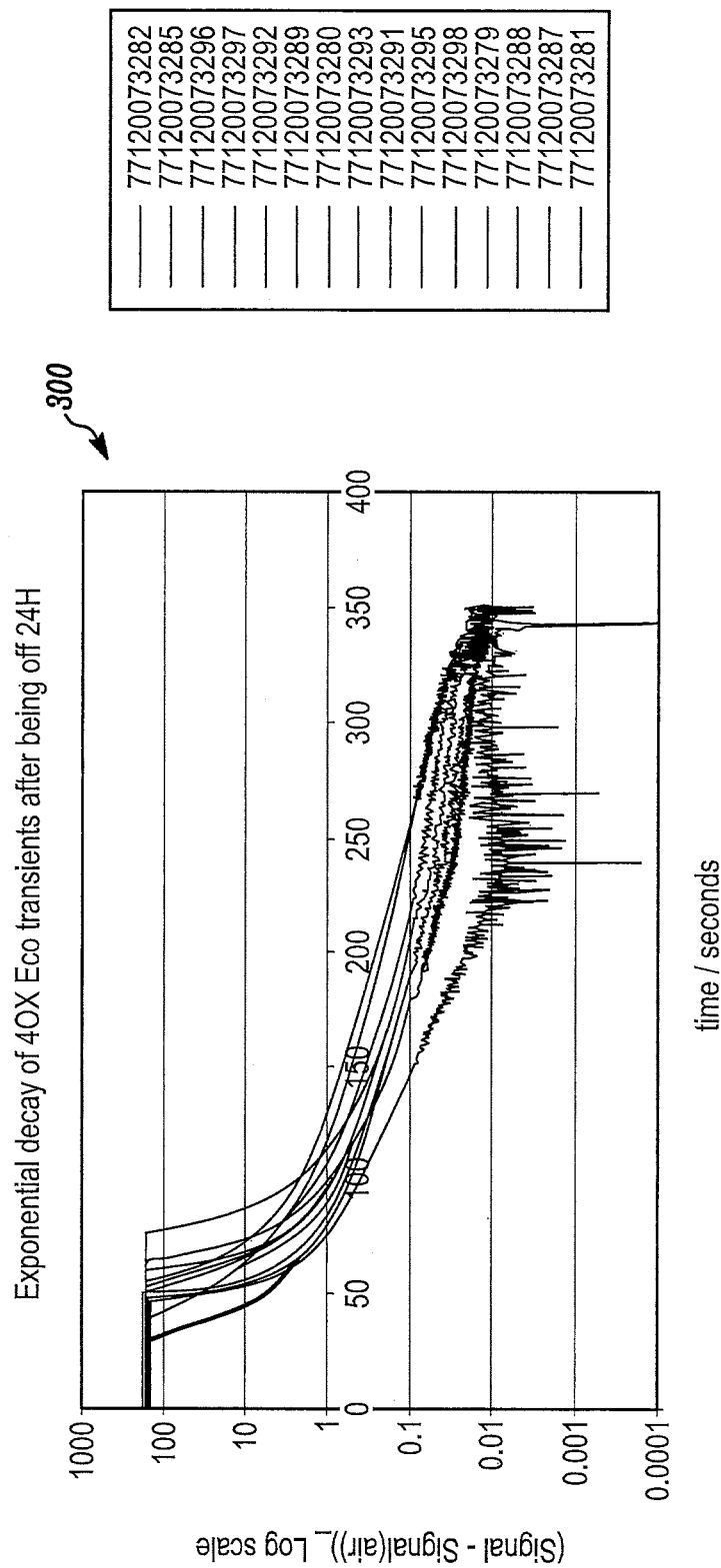
FIG. 3 is a graph that includes data from the graph in FIG. 1, plotted on a log scale.

While this invention is susceptible of an embodiment in many different forms, there are shown in the drawings and will be described herein in detail specific embodiments thereof with the understanding that the present disclosure is to be considered as an exemplification of the principles of the invention. It is not intended to limit the invention to the specific illustrated embodiments.

Some embodiments disclosed herein are discussed with respect to oxygen pump sensors. However, it is to be understood that embodiments are not so limited. For example, embodiments disclosed herein can be applied to and used in connection with any type of electrochemical sensor that has a prolonged startup time.

Figure 4:
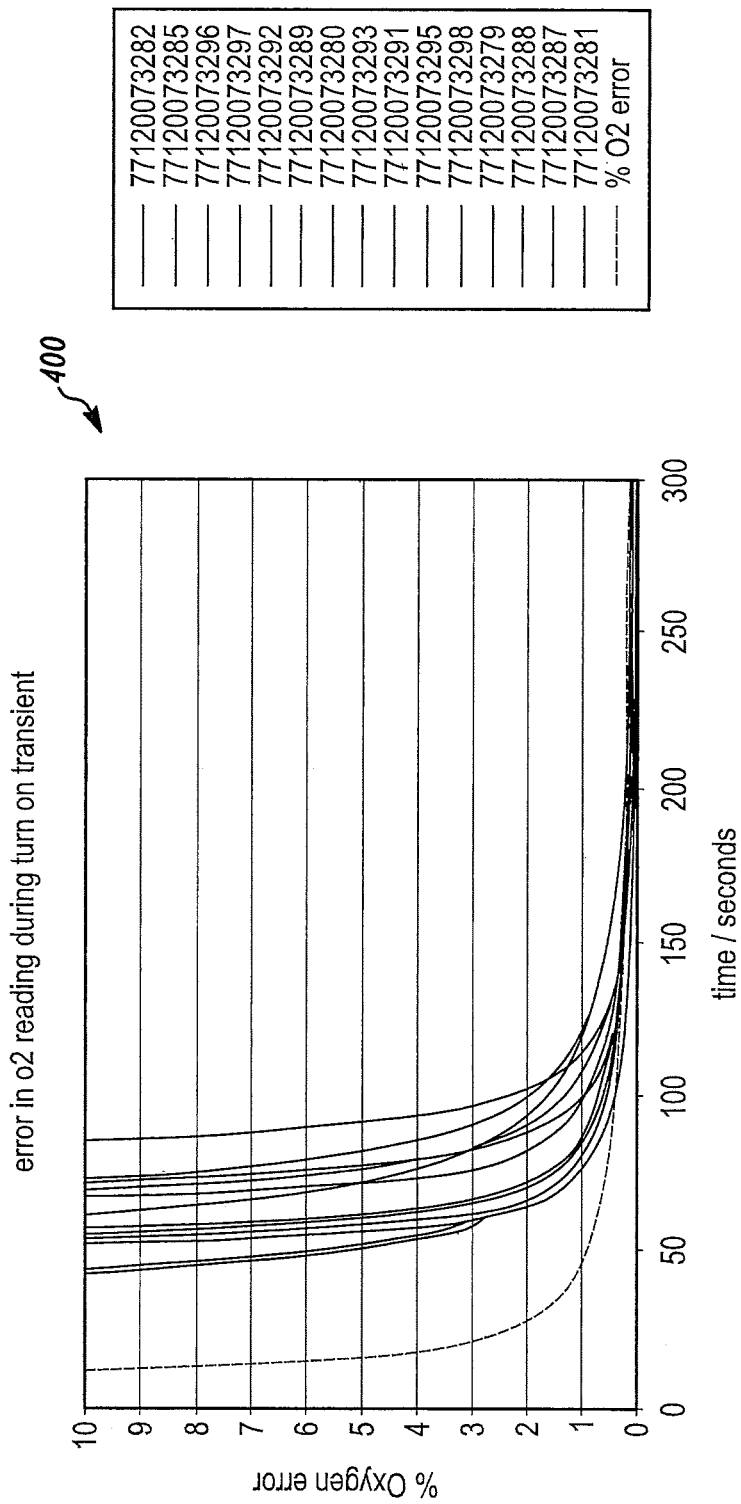
FIG. 4 is a graph that illustrates the startup transient behavior of an electrochemical sensor without any electronic limitations where the sensor has been off load for multiple days.
Figure 5:
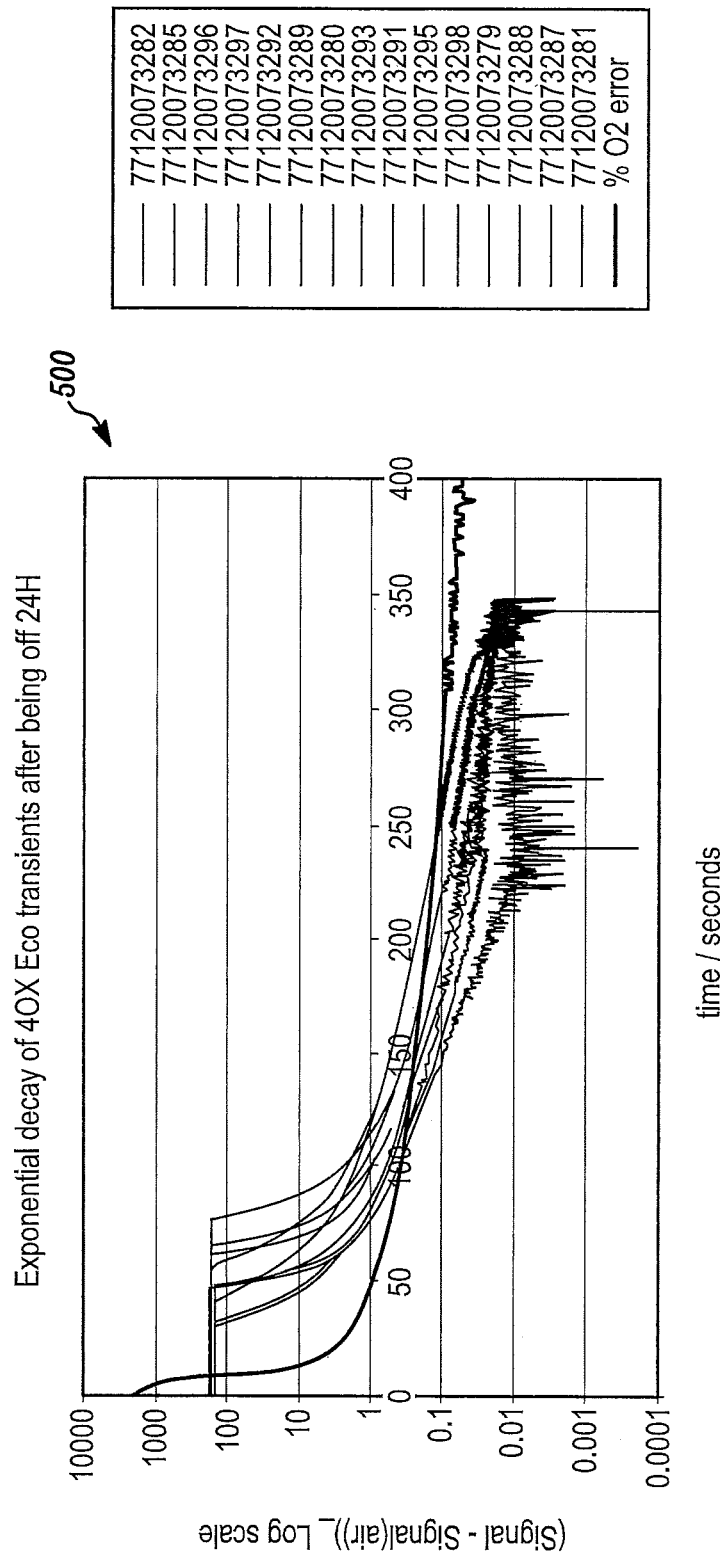
FIG. 5 is a graph that includes data from the graph in FIG. 4, plotted on a log scale.

FIG. 4 is a graph 400 that illustrates the startup transient behavior of an electrochemical sensor without any electronic limitations where the sensor has been off load for multiple days, and FIG. 5 is a graph 500 that includes the data from the graph 400 plotted on a log scale. For example, the sensor whose behavior is illustrated in FIGS. 4 and 5 can have no current limitation, a peak current of approximately 40 mA, and no series resistor. As seen in FIG. 5, when a perfect potentiostat circuit, that is, one that does not include any electronic limitations, operates on a laboratory electrochemical workstation with greater than 1 A current capacity, the circuit can avoid initial saturation and allow first order exponential decay behavior to be reached more quickly as compared to known sensors and circuits. For example, the first order exponential decay behavior can start at approximately 100 seconds, but the error in the air is down to approximately 0.3% oxygen. Accordingly, as seen in FIG. 4, the stabilization or settling time for an electrochemical sensor that includes a perfect potentiostat circuit can be quicker as compared to known sensors and circuits.

While sensors and circuits whose behaviors are illustrated in FIGS. 4 and 5 do not have any electronic limitations, real world sensors and circuits do have such limitations, and a significant contributing factor to the slow startup of oxygen pump sensors is the electronics used in known potentiostat circuits. For example, the electronics in known potentiostat circuits do not provide enough current to rapidly charge the sensor's double layer capacitance and/or to rapidly consume gas that has built up in the sensor while off load. This is particularly true when such potentiostat circuits are run off of a 3V power supply. Accordingly, it can take several minutes or even tens of minutes for the sensing electrode to be driven to the correct operating potential relative to the reference electrode, resulting in the consumption of residual oxygen in the sensor at a slower rate and thereby further extending the settling time.

Various issues can result in the electronic limitations of potentiostat circuits. For example, the current follower can become saturated, the series resistor in the circuit, typically included for stability, can slow down the speed of gas response, operational amplifiers can have current and/or power limits, and supply voltage power supplies can have limitations. For example, known current followers require a split rail power supply, which limits the headroom for driving the counter electrode in the circuit.

To address the deficiencies discussed above as well as others known by those of ordinary skill in the art, embodiments disclosed herein include an electrochemical gas sensor and/or an oxygen pump sensor that includes an improved potentiostat circuit and/or a separate high current booster. For example, in disclosed embodiments, the improved potentiostat circuit and/or the separate high current booster can rapidly drive the sensor to its correct operating potential, thereby reducing the startup time of the sensor from tens of minutes to less than one minute. In some embodiments, the improved potentiostat circuit and/or the separate high current booster disclosed herein can also facilitate the sensor appropriately reacting to nitrogen and/or low oxygen concentration shortly after powering up so that the sensor can be usable as soon as possible after powering up.

In some embodiments, the improved potentiostat circuit and/or the high current booster can boost the current driven into the counter electrode with, for example, a boosted potentiostat circuit or a one shot circuit that can be based on a low dropout voltage regulator to drive the counter electrode until the reference electrode reaches the correct potential, at which point the boosted potentiostat circuit or the one shot circuit can be turned off and the conventional potentiostat circuit can operate.

Figure 6:
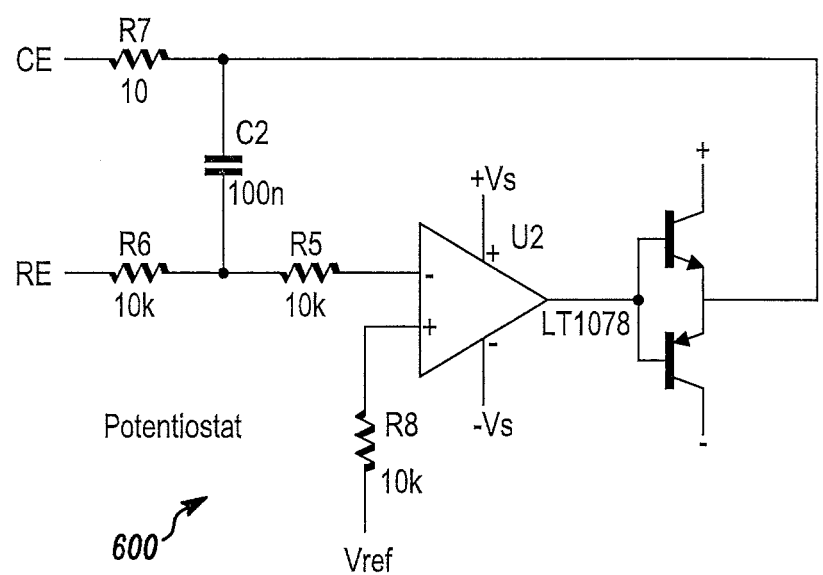
FIG. 6 is a circuit diagram of a potentiostat circuit with a current booster circuit in accordance with disclosed embodiments.
Figure 6A:
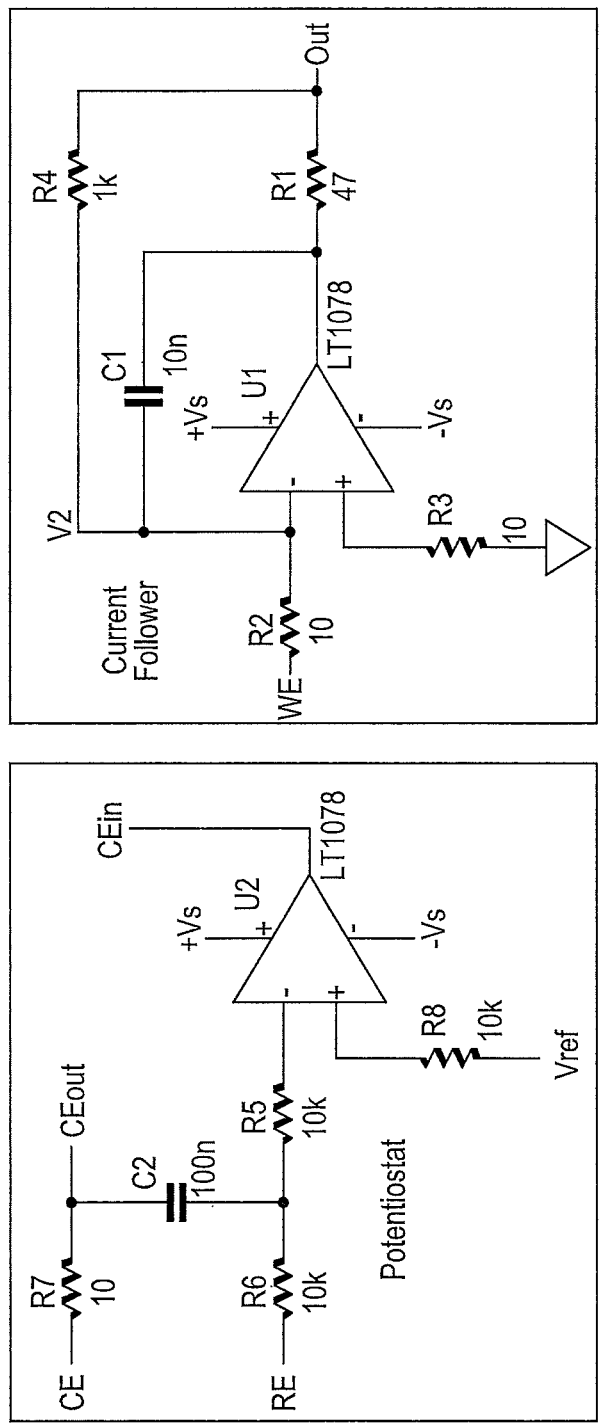
FIG. 6A is a circuit diagram of an alternative current booster circuit that provides a boosted current in only one polarity in accordance with disclosed embodiments.
Figure 6A:
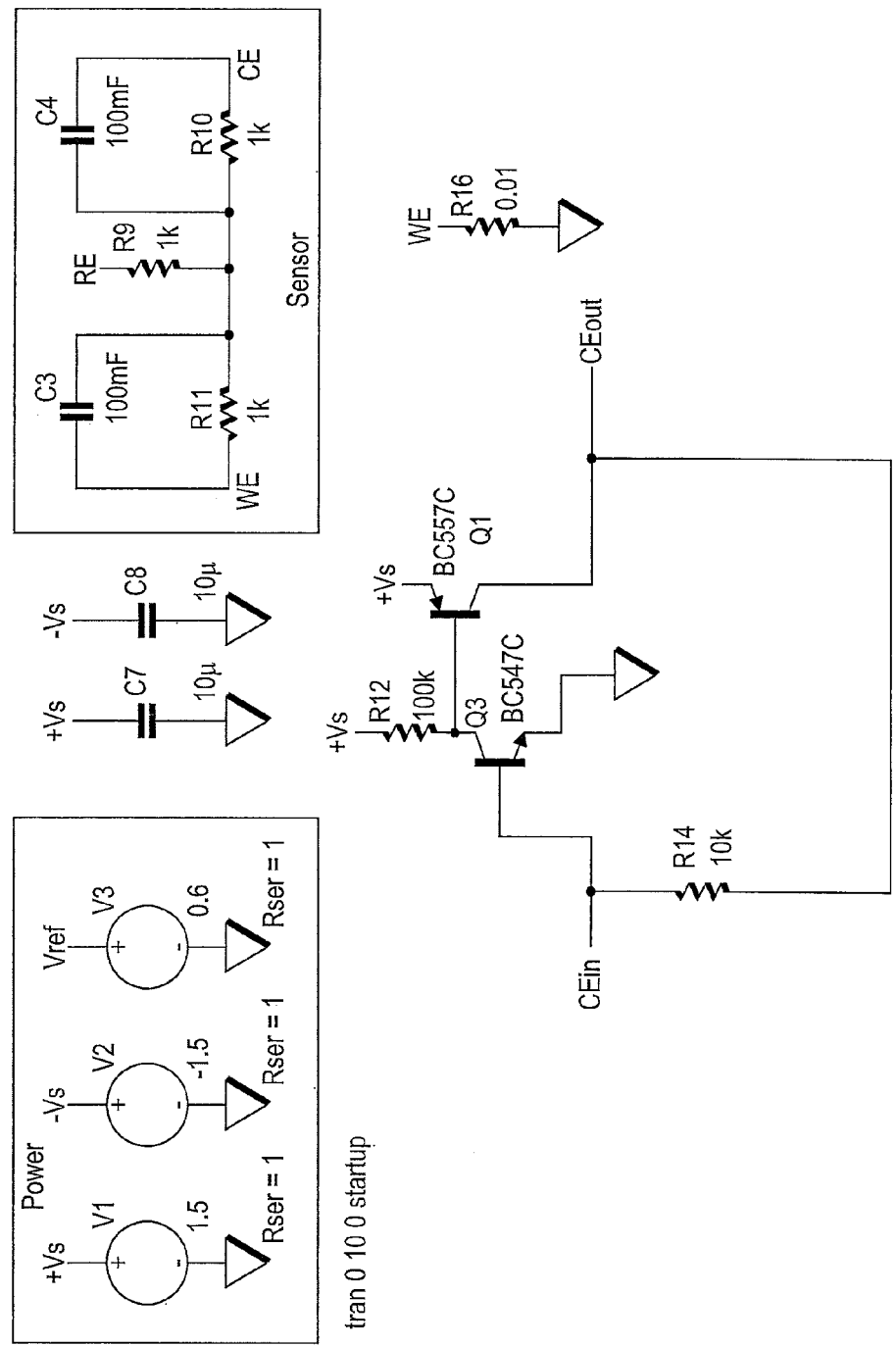

FIG. 6 is a circuit diagram of a potentiostat circuit with a current booster circuit 600 in accordance with disclosed embodiments. As seen in FIG. 6, the circuit 600 can include a push pull output stage that allows a high current to be passed for both positive and negative signals. FIG. 6A is a circuit diagram of an alternative current booster circuit that provides a boosted current in only one polarity in accordance with disclosed embodiments. As seen in FIG. 6A, the current booster can switch in when output exceeds a predetermined value, such as a value that is close to a saturation value.

In disclosed embodiments, the current booster can include at least two transistors inside of the feedback loop: the first transistor can turn on when output exceeds the predetermined value, and the first transistor can turn on the second transistor. When the second transistor is turned on, current can be fed directly to the counter electrode, bypassing a series resistor. However, when the second transistor is not turned on, the potentiostat circuit can operate normally. In some embodiments, the circuit only allows a high current to pass in one direction because, for startup of an oxygen pump sensor, it is only necessary to pass a high current in one direction.

Figure 7:
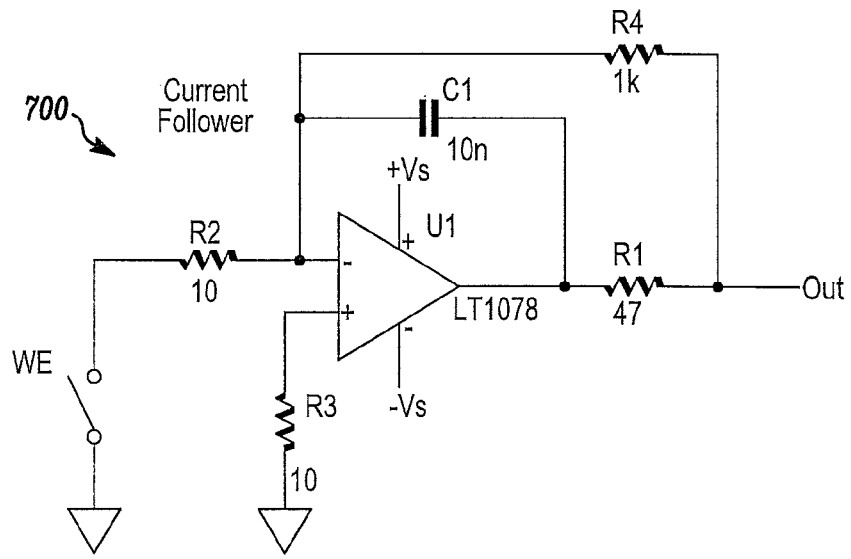
FIG. 7 is a circuit diagram of a current follower circuit in accordance with disclosed embodiments.

To further address the deficiencies discussed above as well as others known by those of ordinary skill in the art, embodiments disclosed herein can also include modifying a current follower circuit. For example, FIG. 7 is a circuit diagram of a current follower circuit 700 in accordance with disclosed embodiments. As seen in FIG. 7, the current follower circuit 700 can include a shorting switch for the sensing electrode. For example, a high current, for example, a current as high as 100 mA, can flow through a counter/sensing electrode circuit to rapidly stabilize a sensor of which the circuit is a part. To achieve this result, the sensing electrode current follower and/or the load resistor can be shorted to maintain zero volts at the sensing electrode, and the sensing electrode can be unshorted when current is sufficiently low so as not to overload the current follower. In some embodiments, the shorting switch can include, but is not limited to, for example, a physical mechanical switch, a relay, or a solid state switch, such as a transistor.

Figure 8A:
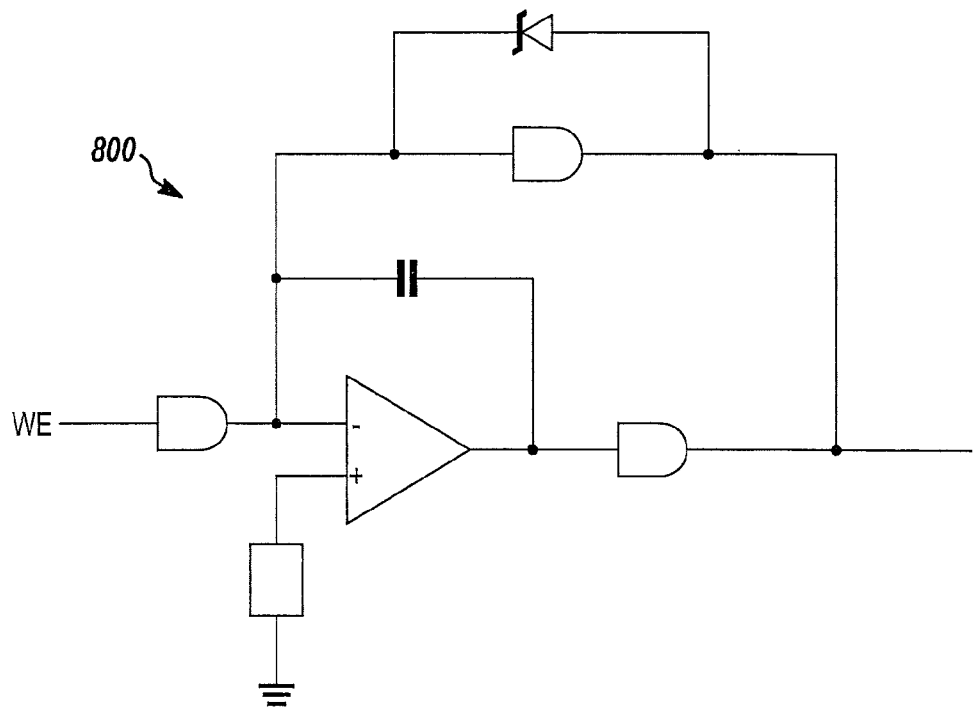
FIG. 8A is a circuit diagram of a current follower circuit that includes a Zener diode across a feedback resistor in accordance with disclosed embodiments.

Some embodiments disclosed herein can be implemented with a current follower modification. For example, FIG. 8A is a circuit diagram of a current booster circuit 800 that includes a Zener diode across a feedback resistor. As seen in FIG. 8A, the Zener diode can allow the feedback resistor to be bypassed when the voltage across the feedback resistor exceeds the Zener voltage, thereby preventing the operational amplifier from saturating.

Figure 8B:
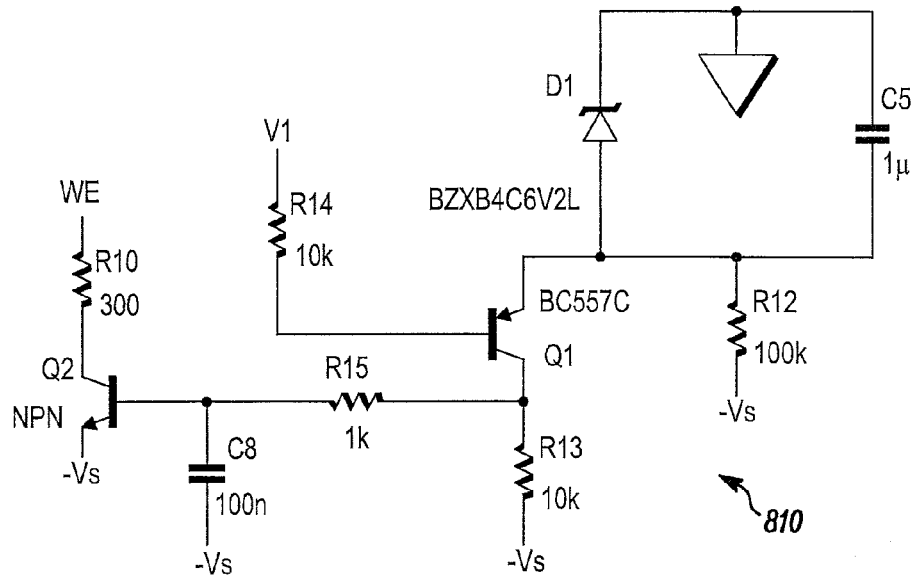
FIG. 8B is a circuit diagram of a current follower circuit that allows a high current to flow which is not limited by the operational amplifier output current and which can optionally bypass the sensing electrode series resistor in accordance with disclosed embodiments.

FIG. 8B is a circuit diagram of a current follower circuit 810 that can allow the sensing electrode series resistor to be bypassed and that can allow a higher current to be passed during startup than is achievable from the current follower alone. As seen in FIG. 8B, the current follower circuit 810 can switch in when output exceeds a predetermined value at which the operational amplifier output is saturated. Transistor Q1 can turn on when output exceeds a predetermined value set by the Zener diode, and transistor Q1 can turn on transistor Q2. Transistor Q2 can feed current directly to the sensing electrode, thereby bypassing the feedback resistor and the series resistor and passing more current than the operational amplifier itself can provide.

In some embodiments, the current follower circuit can be shorted out during startup. For example, the sensing electrode can be shorted directly to the ground during startup, thereby preventing issues that arise due to limitations in the current follower circuit. In some embodiments, a mechanical switch can be employed, and the switch can be closed when turning on power, thereby shorting the current follower. The reference potential can be stabilized, and then the switch can be opened so that the current follower can measure the sensor. In some embodiments, shorting can be performed automatically by employing an FET transistor instead of a mechanical switch. For example, the FET transistor can be on until bias is achieved. Then, the FET transistor can be turned off, output can be checked for saturation, and if saturated, the FET transistor can be turned on again. This process can be repeated until the reference potential is stabilized.

To further address the deficiencies discussed above as well as others known by those of ordinary skill in the art, embodiments disclosed herein can include a single rail power supply. For example, a single rail power supply can be achieved by measuring output voltage across a load resistor instead of a current follower. That is, the load resistor can be used for current measurement instead of the current follower, thereby removing the need for a split rail power supply. In some embodiments, a single rail power supply can be achieved by measuring the current flowing from the counter electrode instead of measuring the current in the sensing electrode circuit, thereby allowing the sensing electrode to be shorted directly to the ground. That is, a high side current measurement can be made using a resistor in series with the counter electrode, thereby providing a faster gas response time and less disturbance of the bias voltage.

In accordance with the above, embodiments disclosed herein can be implemented with current boosters in the counter electrode drive circuit. For example, as explained above, FIG. 6 is a circuit diagram of a potentiostat circuit with a current booster circuit 600 in accordance with disclosed embodiments, and FIG. 7 is a circuit diagram of a current follower circuit 700 in accordance with disclosed embodiments.

In accordance with the above, embodiments disclosed herein can be implemented with separate booster circuits for startup that are in parallel with a known potentiostat circuit. In some embodiments, an adjustable voltage regulator can be used in lieu of a potentiostat circuit. That is, the adjustable voltage regulator can work as the potentiostat circuit. For example, FIG. 9 is a circuit diagram of an adjustable voltage regulator 900 in accordance with disclosed embodiments.

Figure 9:
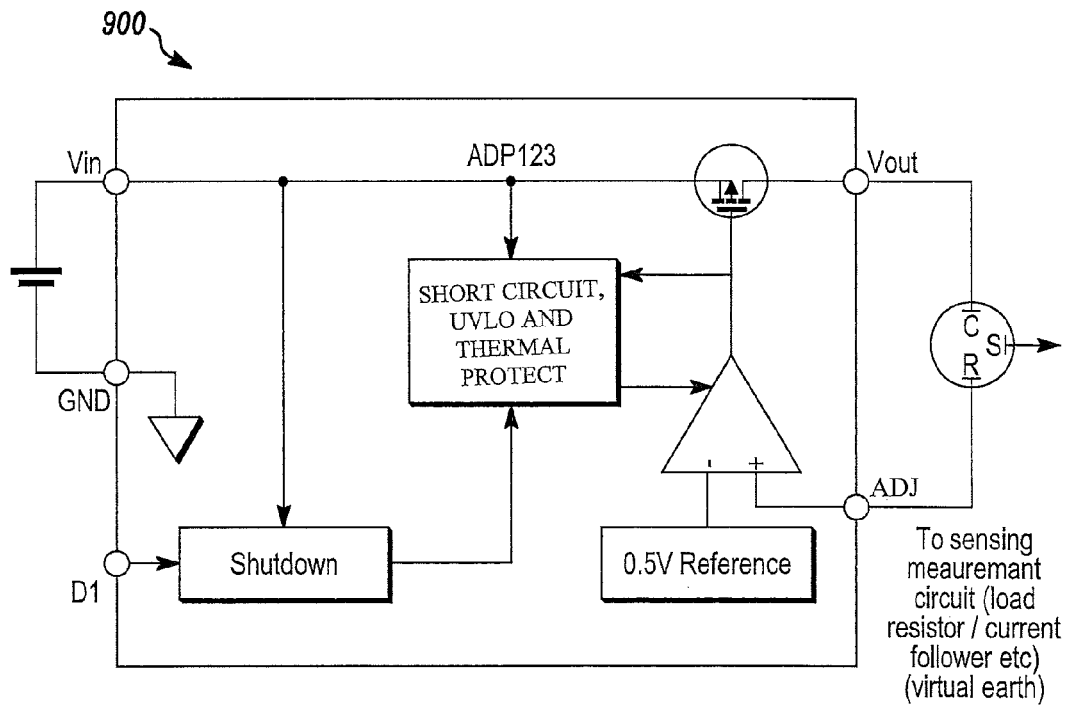
FIG. 9 is a circuit diagram of an adjustable voltage regulator in accordance with disclosed embodiments.

As seen in FIG. 9, the sensing electrode can be grounded, either directly or via a current follower, load resistor, or the like, and the voltage regulator can adjust Vout, the output voltage of the counter electrode, until ADJ input, the reference electrode potential, is equal to the internal reference voltage. Accordingly, the sensor can be potentiostatically controlled with a bias on the sensing electrode relative to the reference electrode. In some embodiments, the reference potential can be adjusted using a buffered resistor divider or amplifier between the reference electrode and the ADJ pin, or by adding an offset voltage to the GND pin in the regulator.

In some embodiments, the adjustable voltage regulator disclosed herein can be used for fast startup in connection with a known potentiostat circuit. For example, the regulator can be turned on for a few seconds during power up to rapidly charge the sensor to a desired reference potential. Then, the regulator can be shut down during normal operation and the potentiostat circuit can drive the sensor as normal.

In accordance with the above, embodiments disclosed herein can be implemented by further accelerating startup time by initially overdriving the counter electrode and then allowing the counter electrode to relax back. For example, voltage at a high current can be applied to the counter electrode until the reference potential reaches a predetermined bias. Then, the applied voltage/current can be switched off, and known potentiostat operation can commence.

In embodiments disclosed herein that include a single rail power supply, various methods in accordance with disclosed embodiments can be employed to measure sensor current and maximize compliance voltage. For example, voltage across a small series resistor can be measured. As explained above, output voltage across a load resistor can be measured instead of using a current follower. As a further example, high side current can be measured. As explained above, current flowing from the counter electrode can be measured instead of measuring the current in the sensing electrode circuit, thereby allowing the sensing electrode to be shorted directly to the ground.

Figure 10A:
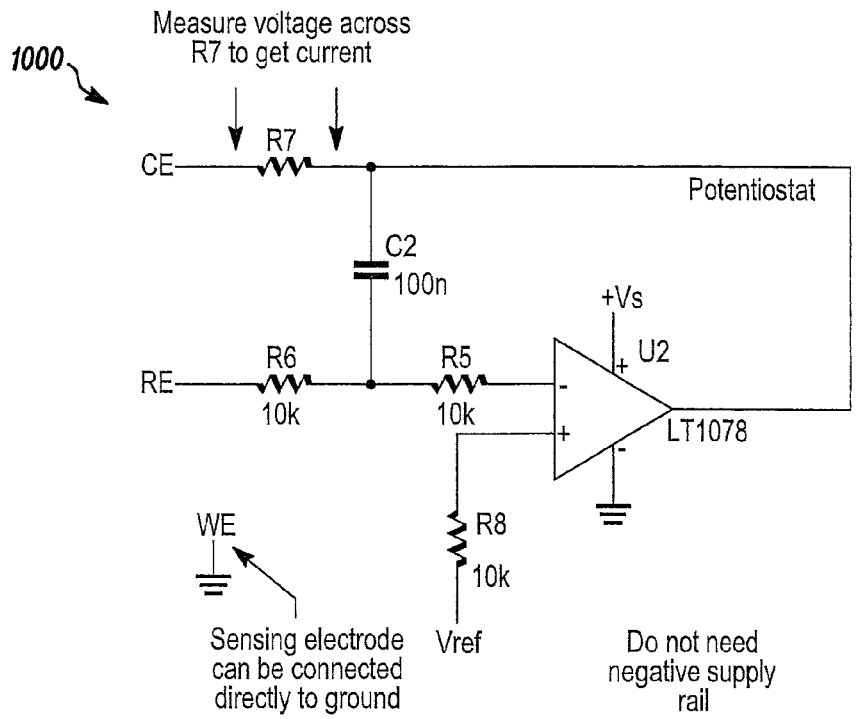
FIG. 10A is a circuit diagram of one embodiment of high side current measurement in accordance with disclosed embodiments.
Figure 10B:
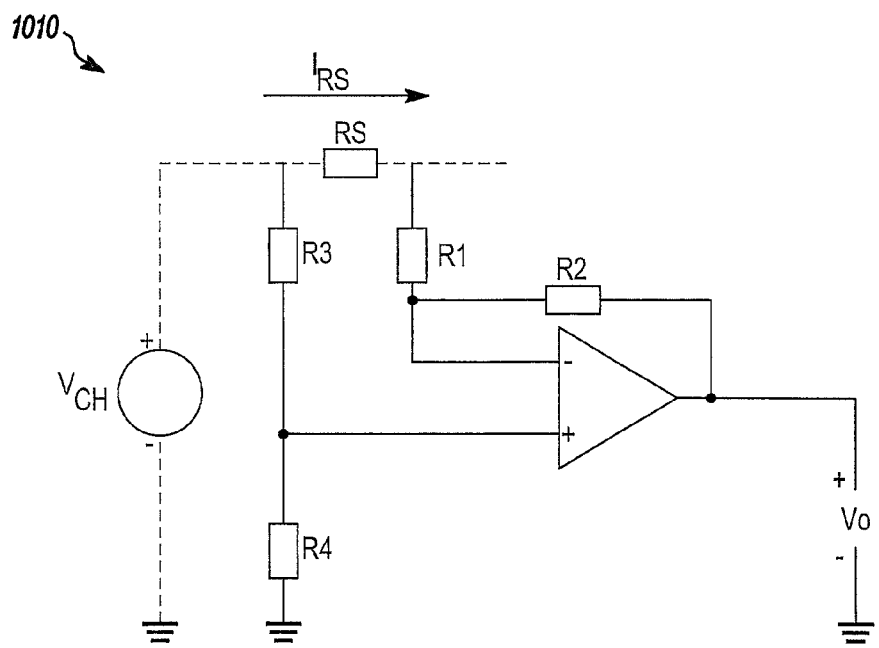
FIG. 10B is a circuit diagram of one embodiment of high side current measurement in accordance with disclosed embodiments.
Figure 10C:
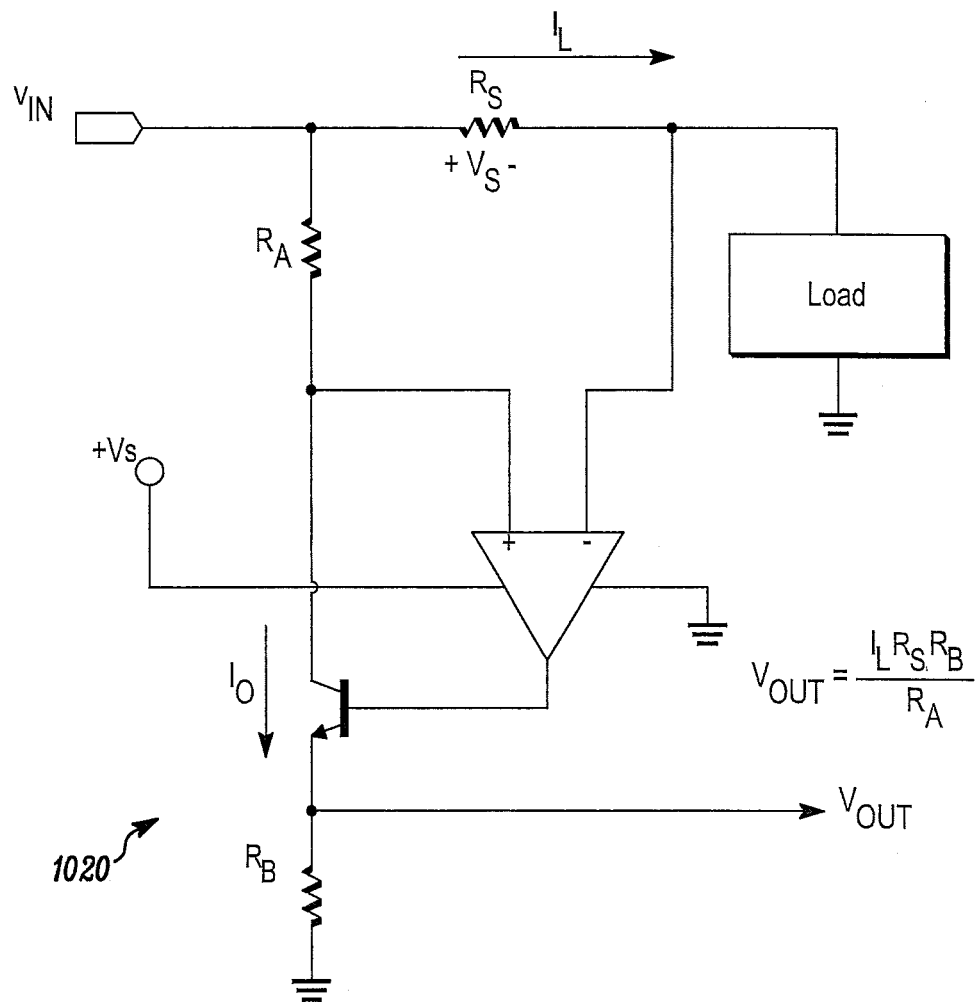
FIG. 10C is a circuit diagram of one embodiment of high side current measurement in accordance with disclosed embodiments.
Figure 10D:
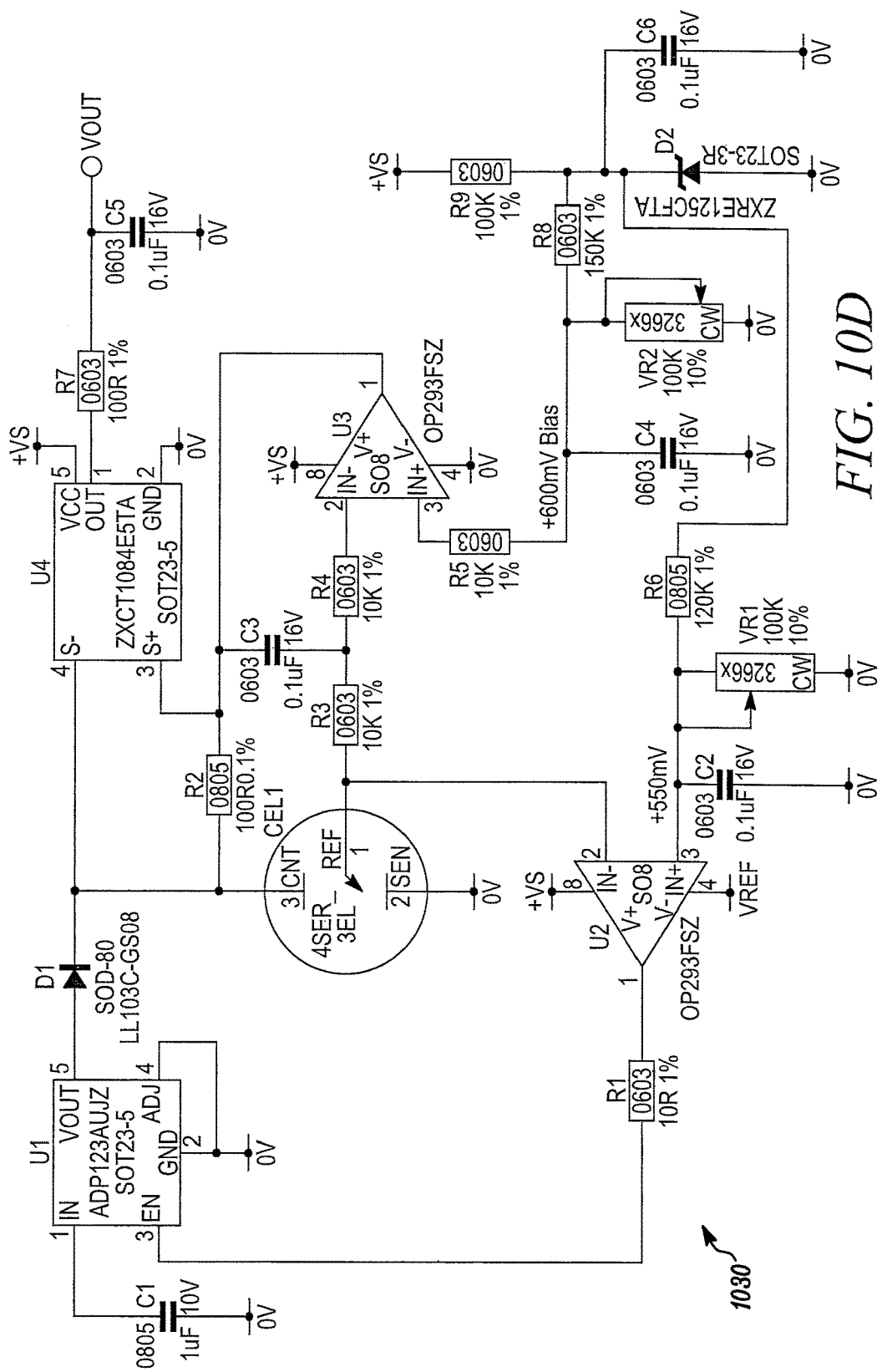
FIG. 10D is a circuit diagram of one embodiment of high side current measurement in accordance with disclosed embodiments.

FIG. 10A is a circuit diagram of one embodiment 1000 of high side current measurement in accordance with disclosed embodiments. For example, voltage can be measured across resistor R7 to determine current. FIG. 10B is a circuit diagram of another embodiment 1010 of high side current measurement in accordance with disclosed embodiments, and FIG. 10C is a circuit diagram of yet another embodiment 1020 of high side current measurement in accordance with disclosed embodiments. Each of the embodiments 1000, 1010, and 1020 includes a resistor Rs in series with the counter electrode. FIG. 10D is also a circuit diagram of an embodiment 1030 of high side current measurement in accordance with disclosed embodiments.

Figure 11:
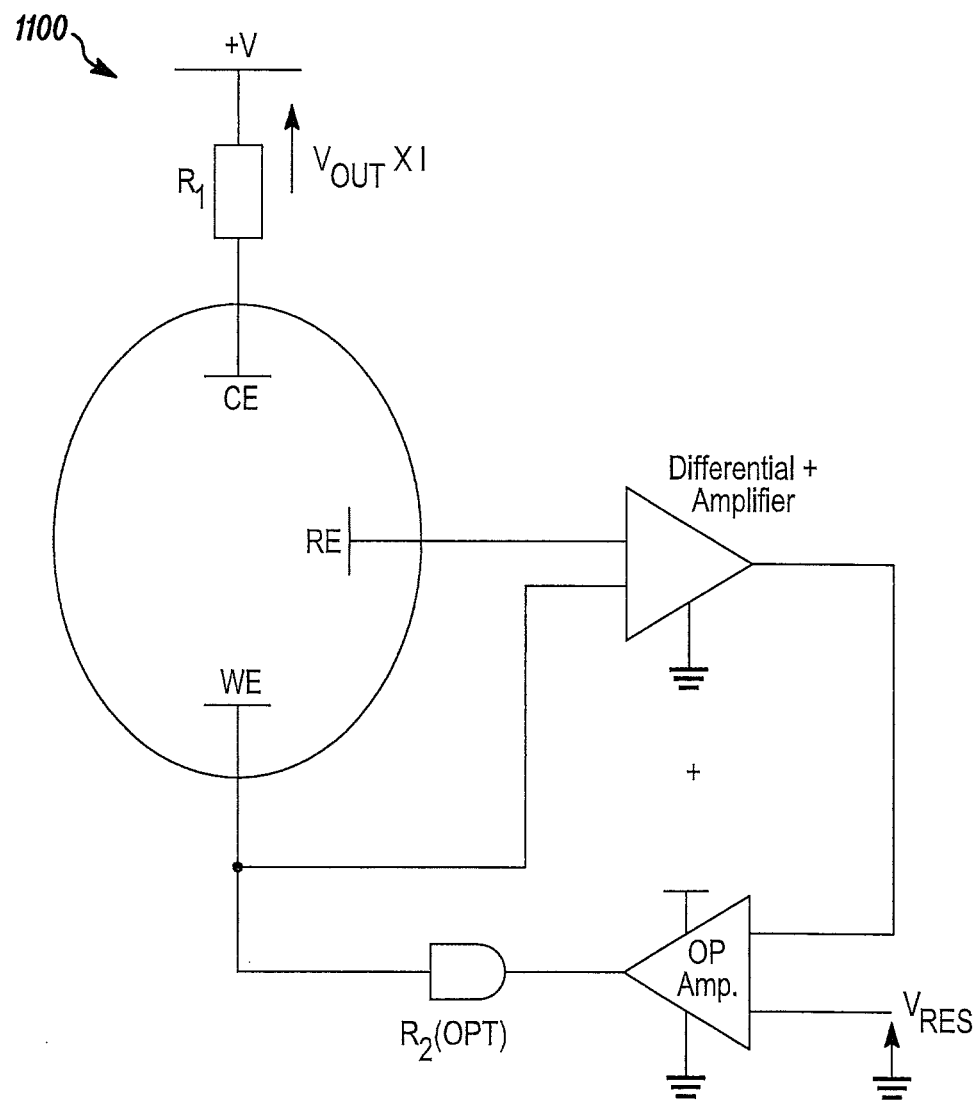
FIG. 11 is a circuit diagram of an embodiment of driving the sensing electrode in accordance with disclosed embodiments.

Finally, in accordance with the above, embodiments disclosed herein can be implemented with an alternative drive method with a counter electrode at a positive rail and varied drive to the sensing electrode. For example, FIG. 11 is a circuit diagram of an embodiment 1100 of driving the sensing electrode in accordance with disclosed embodiments. This embodiment avoids the need for a differential measurement across a current measuring resistor, but requires a differential amplifier to measure voltage between the reference and sensing electrodes and shorting the current measuring resistor R1 during startup.

Although a few embodiments have been described in detail above, other modifications are possible. For example, the logic flows described above do not require the particular order described, or sequential order, to achieve desirable results. Other steps may be provided, or steps may be eliminated, from the described flows, and other components may be added to, or removed from, the described systems. Other embodiments may be within the scope of the invention.

From the foregoing, it will be observed that numerous variations and modifications may be effected without departing from the spirit and scope of the invention. It is to be understood that no limitation with respect to the specific system or method described herein is intended or should be inferred. It is, of course, intended to cover all such modifications as fall within the sprit and scope of the invention.

What is claimed is:
1. A method comprising:
taking an electrochemical oxygen sensor off-load, wherein the electrochemical oxygen sensor comprises a plurality of electrodes, wherein the plurality of elec- trodes comprise a counter electrode, a sensing electrode, and a reference electrode;

powering on the electrochemical oxygen sensor after taking the electrochemical oxygen sensor off-load;

driving the electrochemical oxygen sensor using at least one of a current booster potentiostat circuit or a one shot circuit, using a first amount of current until a reference electrode voltage reaches a bias voltage;

turning the at least one of the current booster potentiostat circuit or the one shot circuit off; and operating the electrochemical oxygen sensor using a potentiostat circuit to detect an oxygen concentration in an ambient gas using a second amount of current after turning the at least one of the current booster potentiostat circuit or the one shot circuit off, wherein the first amount of current is in excess of the second amount of current.

2. The method of claim 1, wherein when a plurality of transistors arranged in a feedback loop are on, an electrical connection is formed between a current source and the counter electrode that bypasses a resistor, and when the transistors are off, an electrical connection between the current source and the counter electrode is only present through the resistor.

3. The method of claim 2, further comprising providing a single rail power supply.

4. The method of claim 3, further comprising measuring output voltage across a load resistor via a voltage sensor.

5. The method of claim 3, further comprising measuring a current flowing from the counter electrode via a current sensor, wherein the counter electrode is electrically coupled with the resistor in series, and wherein the sensing electrode is electrically coupled to ground.

6. The method of claim 1, further comprising adjusting an output voltage of the counter electrode so that a potential of the reference electrode is equal to an internal reference voltage via a voltage regulator configured to provide a variable outlet voltage.

7. The method of claim 6, wherein the voltage regulator arranged in parallel with the potentiostat circuit.

8. The method of claim 1, wherein driving the electrochemical oxygen sensor using the at least one of the current booster potentiostat circuit or the one shot circuit comprises boosting current driven into the counter electrode of the electrochemical oxygen sensor.

9. The method of claim 8, further comprising feeding the second amount of current directly to the sensing electrode of the electrochemical oxygen sensor.

10. The method of claim 1, further comprising shorting the sensing electrode in the electrochemical oxygen sensor; and maintaining zero volts at the sensing electrode in response to the shorting.

11. The method of claim 1, further comprising providing a single rail power supply.

12. The method of claim 11, further comprising measuring output voltage across a load resistor.

13. The method of claim 11, further comprising measuring a current flowing from the counter electrode, wherein the counter electrode is electrically coupled with a resistor in series, and wherein the sensing electrode is electrically coupled to ground.

14. The method of claim 1, wherein operating the electrochemical oxygen sensor using the potentiostat circuit comprises: potentiostatically controlling a bias on the sensing electrode in the electrochemical oxygen sensor relative to the reference electrode in the electrochemical oxygen sensor with a voltage regulator, wherein the voltage regulator provides a variable outlet voltage.

15. The method of claim 1, wherein driving the electrochemical oxygen sensor using the at least one of the current booster potentiostat circuit or the one shot circuit comprises overdriving a counter electrode in the electrochemical oxygen sensor until a reference potential reaches the bias voltage.

* * * * *

UNITED STATES PATENT AND TRADEMARK OFFICE
CERTIFICATE OF CORRECTION

PATENT NO. : 10,054,564 B2
APPLICATION NO. : 13/944375
DATED : August 21, 2018
INVENTOR(S) : Keith Francis Edwin Pratt and Ali Hosseinmardi Page 1 of 1

It is certified that error appears in the above-identified patent and that said Letters Patent is hereby corrected as shown below:

In the Specification

Column 3/Line 11: "1 A" should be "1A"

Signed and Sealed this
Twenty-seventh Day of November, 2018

Andrei Iancu
*Director of the United States Patent and Trademark Office*